United States Patent [19]

Chirchirillo et al.

[11] Patent Number: 4,693,889

[45] Date of Patent: Sep. 15, 1987

[54] BIRD REPELLENT COMPOSITION

[75] Inventors: Michael T. Chirchirillo; Terrance Cannan, both of Chicago, Ill.

[73] Assignee: Velsicol Chemical Corporation, Rosemont, Ill.

[21] Appl. No.: 806,877

[22] Filed: Dec. 9, 1985

[51] Int. Cl.$^4$ ............................................ A61K 31/745
[52] U.S. Cl. ...................................... 424/83; 514/918
[58] Field of Search ............................................ 424/83

[56] References Cited

U.S. PATENT DOCUMENTS 3,734,875  5/1973  Sekuler ................................ 514/762
3,894,039  7/1975  Hiltmann et al. ...................... 424/84

OTHER PUBLICATIONS

Chemical Abstracts; vol. 86 (1977), #56522q; Kiselev.

Primary Examiner—Leonard Schenkman
Assistant Examiner—Joseph A. Lipovsky
Attorney, Agent, or Firm—Lockwood, Alex, FitzGibbon & Cummings

[57] ABSTRACT

This invention relates to bird repellent. In particular, this invention relates to new compositions for protecting surfaces from birds and to repelling birds from various areas. It is also directed to a method of preventing birds from remaining in selected areas.

7 Claims, No Drawings

BIRD REPELLENT COMPOSITION

The problems caused by the presence of birds such as pigeons and starlings in various locations, particularly from their resting places on public buildings are numerous. The need to constantly clean these buildings is high and very costly. Furthermore, the presence of the birds causes people to avoid the areas.

Various devices have been used to prevent the birds from resting on the buildings and other areas where they are not wanted. Usually, the birds adapt quickly to the presence of the devices and render them useless for their intended function.

Also, various compositions have been prepared and used to prevent the birds from resting on the buildings and other locations. Unfortunately, the compositions themselves render the buildings and other locations discolored and in such a condition that the cure is little better than the presence of the birds.

Therefore, it is an object of the present invention to prepare new compositions that will repel birds and not discolor or otherwise injure the location to which they are applied to repel the birds.

Another object of the present invention is to devise a method of repelling birds without damaging the area to which the composition is applied.

Other objects will become apparent from the ensuing description.

It is now being found possible to prepare compositions that repel birds and do not stain or otherwise disfigure the area to which they are applied. These compositions differ substantially from the presently used compositions, particularly in the fact that when applied to the surface to prevent the birds from staying where they are not desired, the surface is not defaced by the composition. One of the causes of this defacing of the buildings and other surfaces where birds tend to rest is the leaking of the oil contained in the bird repellent composition.

The new compositions of this invention are as follows:

| Component | Weight Percent |
|---|---|
| Polyisobutylene | 15-35% |
| Paraffin Oil | 20-50% |
| Isoparaffin Oil | 0-15% |
| Organic Modified Montmorillonite | 0-6% |
| Kaolin Clay | 15-45% |

It is preferred that there be present a minimum of about 5 weight percent isoparaffin oil and a minimum of about 5 weight percent of the organic modified montmorillonite. A more preferred composition within the scope of the present invention has the following components:

| Component | Weight Percent |
|---|---|
| Polyisobutylene | 20-30% |
| Paraffin Oil | 25-40% |
| Isoparaffin Oil | 5-15% |
| Organic Modified Montmorillonite | 2-5% |
| Kaolin Clay | 15-25% |

These compositions can be prepared by incorporating the organic modified montmorillonite into a solution containing the isoparaffin oil and the paraffin oil and mixing until a gel is obtained. Then the polyisobutylene is added and thoroughly mixed into the gel, preferably with the use of heat to soften the polyisobutylene. The final step in the preferred procedure is to add the kaolin clay to the mixture by mixing until a uniform product is obtained. Other procedures can be used to prepare these new compositions.

In addition to lessening the amount of defacing to the structure to which the bird repellent compositions are placed, the present compositions have an improved shelf life. Other advantages, including ease of application, are obtained by the use of the new compositions.

In accordance with the present invention, the bird repellent compositions are applied to the locus where the birds are to be repelled in ribbons sufficient so that the birds will not remain.

The bird repellent composition of the present invention can be applied by means of a caulking gun by placing the product in the caulking cartridge in an amount depending on the area to be treated. Repeated applications can be made as necessary. This technique and equipment is well known.

The polyisobutylenes useful in the present invention have a low molecular weight, i.e., a Staudinger molecular weight of about 8,000 to 15,000, preferably 10,000-13,000.

EXAMPLE 1

Using the procedures described hereinabove, the following composition was made and tested.

| Component | Weight Percent |
|---|---|
| Polyisobutylene (Vistanex LM-MS) | 25.0 |
| Paraffin Oil (Sunspray) | 38.0 |
| Isoparaffin Oil (Isopar M) | 12.0 |
| Organic Modified Montmorillonite (Bentone SD-1) | 5.00 |
| Kaolin Clay (Huber 80 Clay) | 20.0 |

TABLE 1

| Property | Test Result |
|---|---|
| Initial Tack | Good |
| Water Resistance | Very Good |
| Absorbance | 5.0 cm$^2$ |
| Viscosity | |
| @ room temperature | Good |
| 42° F. | Good |
| 122° F. | Good |
| Shelf Life Separation | |
| 3 weeks @ 50° C. | None |
| 3 weeks @ room temperature | None |
| 5 freeze-thaw cycles | None |

TABLE 2

STAIN AND TACK - 3 Weeks After Application

| | STAIN | | TACK | |
|---|---|---|---|---|
| Surface | Room Temperature | 50° C. | Room Temperature | 50° C. |
| Slate | 0.5 cm | 0.2 cm | Excellent | Excellent |
| Brick | 0.5 cm | 0.1 cm | Excellent | Excellent |
| Marble | 0.5 cm | none | Excellent | Excellent |
| Stainless | 0.5 cm | 0.1 cm | Excellent | Excellent |
| Concrete | — | 0.2 cm | — | Excellent |
| Plywood | — | 2.5 cm | — | Excellent |

Test Procedures

The following procedures were used in obtaining the foregoing results.

(1) Water Resistance: A 3.0 gram sample was applied to the inside surface of a 4 ounce wide mouth glass container which was then filled with water to completely submerge the sample. The sample was allowed to stand for 3 days at room temperature and then evaluated for tack and separation.

(2) Absorbance: A 0.50 gram sample was applied to the center of a 9.0 c.m. Whatman Filler Paper #1. The sample was transferred to the oven and exposed to a constant temperature of 100° F. After 6 days the sample was removed and stain measured as the total area of leached material minus initial area of the sample.

(3) Viscosity: Test material was applied through a caulking gun and evaluated for ease of application and ability to remain stationary after application.

(4) Shelf Life Stability: A sample of test material was placed in sealed 8 ounce glass containers and stored at ambient and 50° C. temperatures for 3 weeks. Sample was then evaluated for hydration, tack, body and water resistance.

Stain Evaluation: 12 inch × 8 inch test panels were tested with the test material and set at 45° angle. Separate panels of each were then exposed to a constant temperature of 122° F. and to atmospheric conditions. After 3 weeeks, the samples were evaluated for tack and stain (the distance any leached material had migrated from the initial application site).

Other compositions within the scope of the present condition which have been made by the described procedures are:

| | Component | Weight Percent |
|---|---|---|
| Polyisobutylene | Vistanex LM-MS | 18.92 |
| Paraffin Oil | Murcol 90 Oil | 50.28 |
| Organic Modified Montmorillonite | Bentone 38 | 3.78 |
| Kaolin Clay | Huber 80 clay | 27.02 |

EXAMPLE 3

| | Component | Weight Percent |
|---|---|---|
| Polyisobutylene | Polybintene 122 | 42.23 |
| Organic Modified Montmorillonite | Bentone SD-1 | 2.82 |
| Paraffin Oil | Sunspray 6N Oil | 25.32 |
| Kaolin Clay | Huber 80 clay | 24.63 |
| Isoparaffin Oil | Tenneco 500-100 | 5.00 |

EXAMPLE 4

| | Component | Weight Percent |
|---|---|---|
| Polyisobutylene | Vistanex LM-MS | 29.41 |
| Paraffin Oil | Sunspray 6N Oil | 39.21 |
| Isoparaffin Oil | Tenneco T500-100 | 6.86 |
| Kaolin clay | Huber 80 clay | 24.52 |

EXAMPLE 5

| | Component | Weight Percent |
|---|---|---|
| Polyisobutylene | Vistanex LM-MS | 30.0 |
| Paraffin Oil | Sunspray 6N Oil | 30.0 |
| Isoparaffin Oil | Isopar M | 12.0 |
| Organic Modified Montmorillonite | Bentone SD-1 | 2.0 |
| Kaolin clay | Borden clay | 26.0 |

EXAMPLE 6

| | Component | Weight Percent |
|---|---|---|
| Polyisobutylene | Vistanex LM-MS | 33.16 |
| Paraffin Oil | Sunspray 6N Oil | 37.90 |
| Isoparaffin Oil | Isopar M | 12.10 |
| Kaolin clay | Celite | 16.84 |

EXAMPLE 7

| | Component | Weight Percent |
|---|---|---|
| Polyisobutylene | Vistanex LM-MS | 22.66 |
| Paraffin Oil | Sunspray 6N Oil | 25.90 |
| Isoparaffin Oil | Isopar M | 8.28 |
| Kaolin clay | Talc | 43.16 |

We claim:

1. A bird repellent composition comprising 15-35 weight percent polyisobutylene having a Staudinger molecular weight of about 8,000 to 15,000, 20-50 weight percent paraffin oil, 0-15 weight percent isoparaffin oil, 0-6 weight percent organic modified montomorillonite and 15-45 weight percent kaolin clay.

2. The bird repellent composition of claim 1, wherein there is present a minimum of 5 weight percent of the isoparaffin oil and the organic modified montmorillonite is present in an amount between 2 and about 5 weight percent.

3. The bird repellent composition of claim 1, wherein the polyisobutylene is present in an amount of between 20 and 30 weight percent, the paraffin oil is present in an amount between 20 and 30 percent by weight, the isoparaffin oil is present in an amount between 5 and 15 weight percent, the organic modified montmorillonite is present in an amount between 2 and 5 weight percent and the kaolin clay is present in an amount between 15 and 25 weight percent.

4. The bird repellent composition of claim 1 wherein the polyisobutylene is present in an amount of about 25 weight percent, the paraffin oil is present in an amount of about 38 weight percent, the isoparaffin oil present in an amount of about 12 weight percent, the organic modified montmorillonite is present in an amount of about 5 weight percent and the kaolin clay is present in an amount of about 20 weight percent.

5. The method of repelling bids which comprises applying to the locus where the birds are to be repelled the bird repellent composition of claim 1.

6. The method of claim 5 wherein the bird repellent composition of claim 3 is applied to the locus where the birds are to be repelled.

7. The method of claim 5 wherein the bird repellent composition of claim 4 is applied to the locus where the birds are to be repelled.

* * * * *